United States Patent [19]
Fukunaga

[11] Patent Number: 5,847,835
[45] Date of Patent: Dec. 8, 1998

[54] OPTICAL ABSORBANCE METER

[75] Inventor: Shingo Fukunaga, Tokuyama, Japan

[73] Assignee: Tosoh Corporation, Shinnanyo, Japan

[21] Appl. No.: 824,094

[22] Filed: Mar. 25, 1997

[30] Foreign Application Priority Data

Mar. 29, 1996 [JP] Japan .................................. 8-076682

[51] Int. Cl.[6] .............................. G01N 1/10; G01N 21/00
[52] U.S. Cl. .......................... 356/436; 356/440; 356/246
[58] Field of Search .................................. 356/432, 436, 356/440, 246

[56] References Cited

U.S. PATENT DOCUMENTS

| | | |
|---|---|---|
| 3,516,752 | 6/1970 | Hrdina . |
| 3,954,341 | 5/1976 | Uffenheimer . |
| 4,011,451 | 3/1977 | Nelson ..................................... 356/246 |
| 4,019,372 | 4/1977 | Parkell, et al. . |
| 4,886,356 | 12/1989 | Paradis ..................................... 356/440 |
| 5,153,679 | 10/1992 | Gilby ..................................... 356/440 |

FOREIGN PATENT DOCUMENTS 0 626 574  11/1994  European Pat. Off. .

Primary Examiner—Frank G. Font
Assistant Examiner—Amanda Merlino
Attorney, Agent, or Firm—Oblon, Spivak, McClelland, Maier & Neustadt, P.C.

[57] ABSTRACT

An optical absorbance meter has a flow passage for liquid to be tested, each end of which is closed with a flat light-transmission plate, an introducing path for introducing liquid to the flow passage and a discharging path for discharging the liquid from the flow passage wherein light from a light source is incident from one side near the flat light-transmission plate and emits from the other side near the flat light-transmission plate, wherein a first optical aperture is disposed in front of the flat light-transmission plate at an incident side; a second optical aperture is disposed in rear of the flat light-transmission plate at an emission side; the aperture diameter of the first optical aperture in the direction perpendicular to the axial line of the flow passage is equal to or smaller than the smallest diameter of the flow passage in the direction perpendicular to the axial line of the flow passage, and the aperture diameter of the second optical aperture in the direction perpendicular to the axial line of the flow passage is equal to or larger than that of the first optical aperture.

20 Claims, 2 Drawing Sheets

OPTICAL ABSORBANCE METER

FIELD OF THE INVENTION

The present invention relates to an optical absorbance meter used in a field of liquid chromatography or the like. In particular, the present invention relates to a flow-cell type optical absorbance meter in which liquid is caused to flow to measure the optical absorbance of the liquid.

DISCUSSION OF THE BACKGROUND

In recent years, various analyses have been conducted with use of liquid chromatography. In particular, a high speed liquid chromatography (HPLC) is widely used not only for general analysis but also in a field of clinical diagnosis due to its having excellent speed and separating properties.

In analyzing eluted substances from a column in HPLC and so on, there have been frequently conducted analysis using an optical absorbance meter such as UV detection using an ultraviolet absorbance meter and so on. In particular, a flow-cell type optical absorbance meter in which an eluted substance from the column is permitted to flow to measure the absorbance of the substance, is installed in various kinds of analyzers.

In the liquid chromatography, a sample to be tested is eluted from the column. For the purpose of improving the separating properties and reducing a time of analysis in this case, a so-called gradient analysis is sometimes employed in which two or more kinds of solvents are supplied by changing a proportion or the order of supply. The gradient analysis has such a problem that when a difference between the concentrations of solvents used is large and a difference between the refractive indices of the solvents is large, the layers of the solvents having different refractive indices are formed in the flow passage in the flow-cell type liquid chromatography whereby the base line of the chromatogram varies. The variation of the base line does not indicate a change in the absorbance of the sample to be tested, but a noise indicating a difference between the refractive indices of the solvents. In particular, when the concentration of the sample to be tested is low and the peak in the chromatogram is low, influence caused is not negligible.

In order to solve the problem, there has been proposed a method in which, on the assumption that the same test is repeatedly conducted under the same condition, a typical variation of a base line is previously recorded, and a quantity of variation is subtracted from the chromatogram obtained. In this method, however, a difference of variations of the base line caused by a difference between testing machines to be used and days on which tests are conducted, can not be taken into consideration. Further, the method can not quickly respond when conditions of gradient or conditions of measurements change.

The flow-cell type optical absorbance meter has a flow passage for liquid and a light path for light for testing which are commonly used. In such an optical absorbance meter, there has been known that a change of the base line is proportional to a quantity of light, which is irregularly reflected on the inner wall of the flow passage in a case that a proportion of two or more kinds of solvents is changed, or a certain kind of solvent used is switched to another. To eliminate such disadvantages there has been used a flow-cell (a taper-cell) type having a circular cone-type flow passage in which the diameter of the flow passage at a light emission side is larger than the diameter of the flow passage at a light incident side whereby irregular reflection of light on the inner wall of the flow passage is reduced. However, the taper-cell type involves difficulty in forming the flow passage whereby productivity is low and a large-scale production is difficult. Further, although the taper-cell type can reduce irregular reflection of light on the inner wall of the flow passage when the ratio Y/X, where X represents the diameter of the flow passage at a light incident side and Y represents the diameter of the flow passage at a light emission side, is large, it is generally difficult to reduce X to be 1 mm or lower. On the other hand, when Y is increased, the volume of the flow passage is increased with the result that a response for testing is decreased.

There has been used a flow cell type optical absorbance meter in which a convex lens is disposed at a light incident side to form a focal point of incident light at an end of the flow passage whereby irregular reflection of light on the inner wall of the flow passage is reduced. In this case, however, there is a problem that when a convex lens of low precision of refraction of light at its outer periphery is used, a light path which is different from an intended design is formed and irregular reflection takes place. In addition, if the optical axis of the convex lens is not correctly adjusted, irregular reflection takes place, and accordingly maintenance is required for the device.

In order to prevent the irregular reflection of light on the inner wall of the flow passage, the inner wall of the flow passage for liquid in the flow-cell type optical absorbance meter should not be irradiated with light. For this, it is necessary that light is incident at a very acute angle precisely, or that ideal parallel rays are incident in the flow passage.

However, a precise optical system is needed to realize this. Further, a complicated maintenance is required and productivity is low. Further, it is difficult to satisfy demands for miniaturization for HPLC devices.

In general, light receiving means such as a photodiode or the like is disposed at a light emission side of the flow-cell type flow passage to receive and analyze light passing therethrough. In this case, light emitted through the flow passage is not 100% absorbed by the light receiving means but a substantial portion of light is reflected thereby entering again into the flow passage. Thus, the conventional technique does not provide a solution to eliminate the irregular reflection of light on the inner wall caused by the returning of light from the light emission side.

SUMMARY OF THE INVENTION

It is an object of the present invention to provide an optical absorbance meter having a simple structure and preventing irregular reflection of light on the inner wall of the flow passage.

In accordance with the present invention, there is provided an optical absorbance meter comprising a flow passage for liquid to be tested, each end of which is closed with a convex lens or a flat light-transmission plate, an introducing path for introducing liquid to the flow passage and a discharging path for discharging the liquid from the flow passage wherein light from a light source is incident from one side near the convex lens or the flat light-transmission plate and emits from the other side near the convex lens or the flat light-transmission plate, the optical absorbance meter being characterized in that: a first optical aperture is disposed in front of the convex lens or the flat light-transmission plate at an incident side; a second optical aperture is disposed in rear of the convex lens or the flat light-transmission plate at an emission side; the aperture diameter of the first optical aperture in the direction perpendicular to the axial line of the flow passage is equal to or smaller than the smallest diameter of the flow passage in the direction perpendicular to the axial line of the flow passage, and the aperture diameter of the second optical aperture in the direction perpendicular to the axial line of the flow passage is equal to or larger than that of the first optical aperture.

DESCRIPTION OF THE PREFERRED EMBODIMENTS

Figure 1:
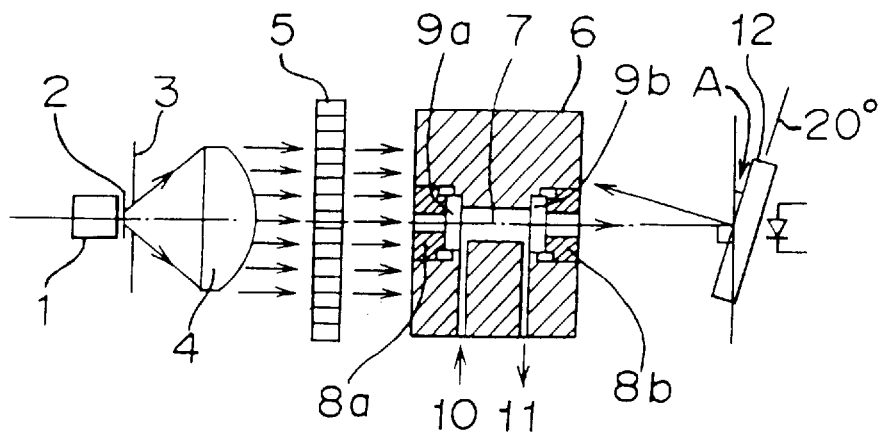
FIG. 1 is a diagram showing an embodiment of the optical absorbance meter according to the present invention.

In the following, preferred embodiments of the optical absorbance meter according to the present invention will be described in detail with reference to the drawings wherein the same reference numerals designate the same or corresponding parts.

FIG. 1 shows an embodiment of the optical absorbance meter according to the present invention. An optical absorbance meter main body 6 comprises a cylindrical space 7 as a flow passage, an introducing path 10 for introducing liquid to the flow passage, a discharging path 11 for discharging the liquid from the flow passage, flat plates 9a, 9b, as closing members for closing ends of the flow passage and first and second optical apertures 8a, 8b which are adapted to fix the flat plates 9a, 9b to the main body 6.

The shape of the flow passage 7 is not in particular limited as far as it does not prevent the introduced liquid from passing and light for testing from passing. For instance, it may have a polygonal shape such as a square pole. Although it may have a tapered flow passage, a cylindrical flow passage is in particular preferable from the standpoint of easiness of machining and productivity.

Figure 3:
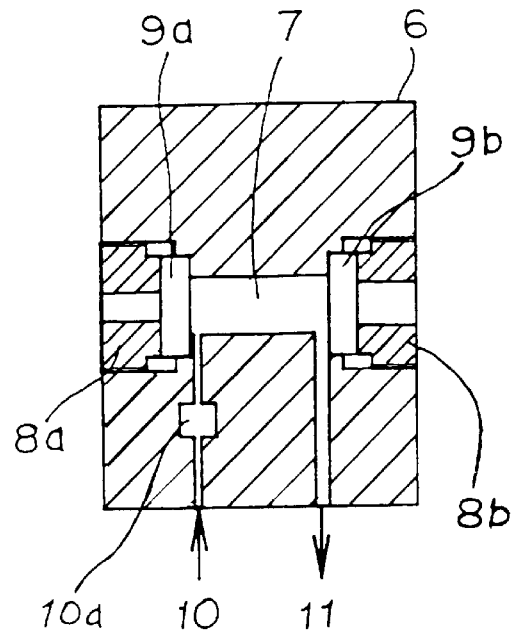
FIG. 3 is a diagram showing a modified embodiment of the optical absorbance meter shown in FIG. 1 according to the present invention.

The flow passage itself is formed with both ends opened. However, the both ends can be closed with the flat plates 9a, 9b which permit light to pass through and which form a closed space. As shown in FIG. 1, the introducing path 10 and the discharging path 11 are formed at portions in the vicinity of the end of the flow passage respectively and on the same side of the main body 6. However, the introducing path 10 and the discharging path 11 may be formed at different sides. A sample liquid supplied from the introducing path 10 to the flow passage is discharged through the discharging path 11 after having been passed through the flow passage 7. It is preferable that the introducing path 10 is provided with a diffusion path which stirs the sample liquid to be introduced. For instance, as shown in FIG. 3, an enlarged diameter portion 10a is formed in a part of the introducing path 10 so that a liquid supply speed is decreased at this portion and a turbulent flow is resulted there whereby the sample liquid is diffused in a form of Gaussian distribution.

Figure 4:
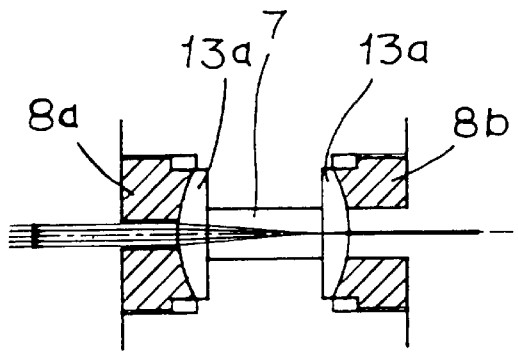
FIG. 4 is a diagram showing an another embodiment of the present invention.

In place of the flat plates 9a, 9b for closing both ends of the flow passage, convex lenses 13a, 13b may be used as shown in FIG. 4. These flat plates 9a, 9b or the convex lenses 13a, 13b are respectively pressed and fixed to the flow passage 7 by means of the first and second optical apertures 8a, 8b. In the present invention, it is not always necessary that the flat plates 9a, 9b or the convex lenses 13a, 13b are pressed and fixed by means of the optical apertures 8a, 8b. However, the construction of this embodiment is preferable because the optical absorbance meter can be formed with a small number of units. Thus, the flow passage 7 having both ends closed by the convex lenses 13a, 13b or the light transmission plates 9a, 9b serves a flow passage for the sample liquid as well as an optical path for light.

Figure 5:
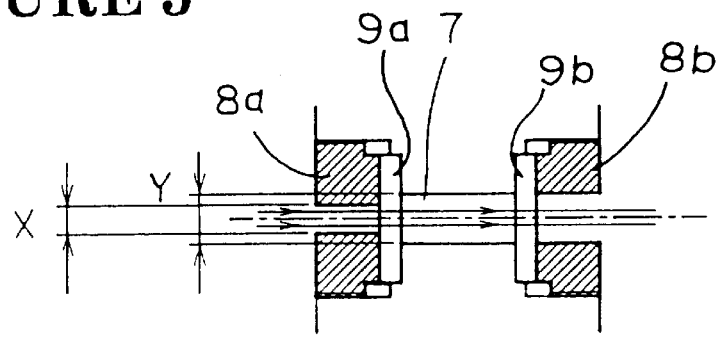
FIG. 5 is a diagram showing a relation between the diameter of the optical aperture X and the diameter of the flow passage Y of the optical absorbance meter of the present invention.

The aperture diameter of the first optical aperture 8a in the direction perpendicular to the axial line of the flow passage 7 is determined to be equal to or smaller than the smallest diameter of the flow passage in the direction perpendicular to the axial line of the flow passage, and the first optical aperture 8a is disposed in such a relation that the axial line is in agreement with the optical axis of the flow passage 7. Namely, the diameter and the shape of the flow passage 7 and the optical aperture 8a should have such a positional relation that the diameter and the shape of the flow passage 7 for passing light fluxes is equal to or larger than the maximum diameter of light fluxes entering from a light incident side of the flow passage to reach a light emission side via the flow passage, and light entering into the flow passage does not irradiate the inner wall of it. In consideration of the above, a cylindrical passage is preferably used because the diameter does not change. In the present invention, it is in particular preferable to constitute the flow passage 7 in a relation of a ratio of Y/X of 1.5 or more wherein X represents the diameter of the optical aperture and Y represents the smallest diameter of the flow passage in the direction perpendicular to the axial line (FIG. 5). For instance, a plate having one or more than two pin holes can be a suitable first optical aperture 8a.

It is preferable that the first optical aperture 8a is disposed just before the convex lens 13a or the flat light-transmission plate 9a located at a light incident side of the flow passage, and more preferably, it approaches the convex lens or the flat plate as possible. It is because a component of light from the light source which does not constitute a parallel light, in particular a component of light causing irregular reflection on the inner wall of the flow passage, can effectively be removed.

The aperture diameter of the second optical aperture 8b in the direction perpendicular to the axial line of the flow passage should be equal to or larger than that of the first optical aperture 8a. Since the second optical aperture serves to prevent light from being incident into the flow passage 7 from a light emission side, it is preferably formed to have a small diameter as possible. More specifically, the optical diameter of the first and second optical apertures 8a, 8b are the same, for instance.

It is also preferable that the second optical aperture 8b is disposed just after the convex lens 13b or the flat light-transmission plate 9b located at a light emission side of the flow passage, and more preferably, it approaches the convex lens or the flat plate as possible, for the purpose, for instance, preventing effectively reflection light reflected on the light receiving means from being incident into the flow passage 7.

The first and second optical apertures 8a, 8b are preferably composed of a black-colored material which exhibits excellent light absorbing properties. In particular, use of optical apertures having a black color and a cylindrical opening as shown in the figure is desirable as the first and second optical apertures 8a, 8b because the optical apertures of cylindrical shape can effectively absorb a non-parallel light component in light from the light source.

Further, other than the optical apertures as shown in the figure, both of or either one of the optical apertures may be subjected to vapor-depositing, printing or coating by masking a material capable of interrupting and/or absorbing light on the convex lens or the flat light-transmission plate.

The optical absorbance meter of the present invention can naturally be constituted as a sole unit independent from other elements. However, it is generally used together with the light source as shown in FIG. 1. An example of such structure will be described with reference to FIG. 1. A light source 1 such as a light-emitting diode is disposed at a light incident side of the optical absorbance meter. A light-diffusion sheet 2 is attached to the light-emitting diode 1. Light from the diode 1 is passed through a pin hole plate 3, the center of which is aligned to the light-emitting point of the diode 1. Then, the light is transformed into light rich in a parallel light component by means of a lens 4, and the transformed light reaches the first optical aperture 8c via an interference filter 5. These elements located at a light incident side should be arranged in vicinity of each other in order to prevent loss of light. In place of attaching the light-diffusion sheet, the front surface of the light-emitting diode 1 is polished with a sand paper to increase the performance effectively.

The light which is rich in a parallel light component is passed through the first optical aperture 8a before entering into the flow passage 7 to be transformed into light fluxes having a smaller diameter than that of the flow passage. As a result, the light reaches a light emission side without causing irregular reflection on the inner wall of the flow passage 7. Of course, the axial center of the optical aperture 8a is in agreement with the optical axis of the flow passage 7. The light emitted through the light emission side is received by the light receiving means 12 such as a photodiode or the like. In a preferred embodiment of the present invention, the light receiving means 12 is disposed with an inclination angle with respect to the light path as shown in FIG. 1, whereby light reflected on the light receiving means 12 is prevented from entering into the flow passage 7 from the light emission side.

In place of the construction described above, a magic mirror or the like which controls the direction of transmittance of light to a specified orientation may be arranged at a light emission side, or an optical system which is in combination of a mirror and a Rayleigh horn may be arranged in a light emission side, whereby it is possible to prevent light from entering into the flow passage 7 from the light emission side.

In particular, emission light can be collected by the Rayleigh horn to be introduced to the light receiving means such as a photodiode. Accordingly, it is possible that light entering into the flow passage 7 by reducing the diameter of the first optical aperture 8a is rendered to a nearly parallel light whereby irregular reflection of light in the flow passage is reduced.

Further, besides the construction as shown in FIG. 1, there may be used such a construction having a light emission means consisting of a sole light source disposed at a light incident side, a light separating means for separating light emitted through the flow passage, a filtering means for permitting only a limited wavelength to pass and a light receiving means for receiving the emitted light disposed at a light emission side of the flow passage. More specifically, the light emission means may comprise a light emission diode which is attached with the light diffusion sheet 2 or which has a front surface polished with a sand paper, a pin hole plate and a lens, and the light receiving means may comprise a dichroic mirror, two different filters and two photodiodes. With this construction, it is possible to provide reference by suitably choosing a dichroic mirror and filters. In constituting a saccharifying hemoglobin measuring device, the first light receiving means is composed of a dichroic mirror and a filter which passes a wavelength in which the absorption peak of a saccharifying hemoglobin component as reference is smallest, and the second light receiving means is composed of a dichroic mirror which reflects light of a wavelength wherein the absorption peak of the saccharifying hemoglobin is the largest and a filter for permitting the wavelength to pass.

An example of the present invention will be described in more detail with reference to the drawing.

However, it should understood that the present invention is by no means restricted by the specific example.

A saccharifying hemoglobin measuring device including the optical absorbance meter shown in FIG. 1 was used. Three kinds of liquid were switchingly supplied according to a step-gradient method, and the behavior of change of the base line caused by switching the supply of the three kinds of liquid was observed.

The particulars of the optical absorbance meter actually used were as follows. The light source system 1 in FIG. 1 was constituted by a light emission diode of ultra high brightness having a wavelength at the center of 450 nm and a half band width of 50 nm in which a front edge of the diode was cut at a portion close to the light source; a light diffusion sheet 2 attached to the front surface of the diode; a plate 3 having a pin hole of 1 mm in diameter which was aligned to the light emission point of the diode; a convex lens 4 having an outer diameter of 10 mm by which light passing through the pin hole plate 3 is transformed into light rich in a parallel light component, and an interference filter 5 disposed at a position 10 mm apart from a light incident side of the optical absorbance meter.

The optical absorbance meter main body 6 was formed to have a cylindrical flow passage 7 of an inner diameter of 1.3 mm and the entire length of 10 mm (i.e., about 13 $\mu$l in volume). Quartz plates 9a, 9b of an outer diameter of 7 mm were fitted to both ends of the flow passage by screw-fitting pressing members 8a, 8b of a hollowed cylindrical shape to the main body 6. The pressing member 8a as the first optical aperture was in a cylindrical shape having an entire length of 5 mm wherein a hollow portion having an inner diameter of 0.8 mm was formed at the center of the cylindrical optical aperture 8a. On the other hand, the pressing member 8b as the second optical aperture was in a cylindrical shape having an entire length of 5 mm wherein a hollow portion having an inner diameter of 1.3 mm was formed at the center of the optical aperture 8b.

The liquid introducing path 10 was connected to a sample introducing device (a sampler) via a pump, and a discharging path 11 was connected to a drain tank.

A light receiving means 12 consisting of a photodiode was disposed 20 mm apart from the optical absorbance meter main body 6 at a light emission side of the flow passage. The photodiode was disposed with an inclination angle of about 20° (A°) with respect to the direction perpendicular to the optical axis of light propagating in the flow passage of the optical absorbance meter so that light reflected on the photodiode does not enter into the flow passage from the light emission side. As a result of observation of a change of the base line, it was found that a change of the base line was $2.2 \times 10^{-4}$ ABU.

Figure 2A:
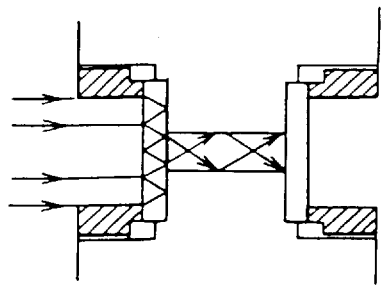
FIGS. 2(a) and 2(b) are diagrams showing a conventional optical absorbance meter.

For comparison, a change of the base line was observed in the same manner as above except that the conventional optical absorbance meter shown in FIG. 2a was used and the light receiving means was disposed in the direction perpendicular to the optical axis of light which propagated in the flow passage. As a result, it was found that a change of the base line was $16.0 \times 10^{-4}$ ABU at the maximum, which was about 8 times as great as that obtained by the optical absorbance meter of the present invention.

The optical absorbance meter shown in FIG. 2a which was actually used was formed to have a cylindrical flow passage having an inner diameter of 1.3 mm and an entire length of 10 mm (about 13 µl in volume), and quartz plates having an outer diameter of 7 mm were fitted to both ends of the flow passage by screw-fitting pressing members of a hollowed cylindrical shape to the main body. Each of the pressing members was formed to have a cylindrical shape having an entire length of 5 mm in which a hollow portion having an inner diameter of 6.5 mm was formed at its center. The pressing members are merely for press-fitting the quartz plates to the main body.

Figure 2B:
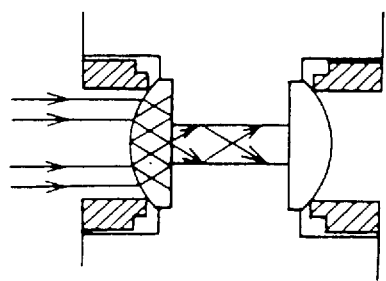

FIG. 2b shows another example of conventional optical absorbance meter wherein convex lenses are used instead of the quartz plates.

In a flow-cell type optical absorbance meter, it is ideal to introduce a completely parallel light into the flow passage whereby irregular reflection of light on the inner wall of the flow passage is prevented. However, in order to realize such an ideal structure, a complicated optical system and frequent maintenance working are necessary, and therefore, the above-mentioned construction is not realistic.

In accordance with the present invention, a first optical aperture having an aperture diameter which is equal to or smaller than the smallest diameter of the flow passage in the direction perpendicular to the axial line of the flow passage, is disposed at a light incident side. Accordingly, it is possible to prevent irregular reflection of light on the inner wall of the flow passage even though a completely parallel light is not introducing into the flow passage. Further, a second optical aperture is disposed at a light emission side of the flow passage whereby irregular reflection of light due to the entering of light from a light emission side is prevented. As a result, a possibility of irregular reflection of light entering into the flow passage of a flow-cell type on the inner wall of the flow passage is reduced. Further, it is possible to reduce a change of the base line even when a proportion of two or more kinds of solvent mixed is changed or even when supply of a certain kind of solvent is switched to another. Further, since the present invention is achieved by contriving the construction of the optical aperture wherein the other elements such as the volume of the flow passage may be the same as the conventional optical absorbance meter, there is no risk of causing a new problem such as reduction of response in testing.

The optical absorbance meter of the present invention can be produced by relatively simple machining and maintenance can be easy.

I claim:

1. An optical absorbance meter including a flow passage for liquid to be tested, each end of which is closed with a respective first and second closing member, an introducing path for introducing liquid to the flow passage and a discharging path for discharging the liquid from the flow passages wherein light from a light source is incident from one side near the first closing member and emits from the other side near the second closing member, the optical absorbance meter comprising:

a first optical aperture disposed in front of the first closing member at an incident side;

a second optical aperture disposed in rear of the second closing member at an emission side; and wherein an aperture diameter of the first optical aperture in a direction perpendicular to an axial line of the flow passage is smaller than a smallest diameter of the flow passage in the direction perpendicular to the axial line of the flow passage, and wherein an aperture diameter of the second optical aperture in the direction perpendicular to the axial line of the flow passage is equal to or larger than that of the first optical aperture.

2. The optical absorbance meter according to claim 1, which further comprises a light emission means composed of a sole light source at a light incident side, a light separating means for forming the spectrum of light emitted from the light emission means or a filtering means for permitting only a limited wavelength to pass, and a light receiving means for receiving light emitted from the flow passage to a light emission side.

3. The optical absorbance meter according to claim 1, which further comprises a light emission means composed of a sole light source at a light incident side, a light separating means for forming the spectrum of light emitted to a light emission side via the flow passage or a filtering means for permitting only a limited wavelength to pass, and a light receiving means for receiving the emitted light.

4. The optical absorbance meter according to claim 2, wherein the light receiving means is disposed so as to be inclined to the optical path of light emitted through the flow passage.

5. The optical absorbance meter according to claim 3, wherein the light receiving means is disposed so as to be inclined to the optical path of light emitted through the flow passage.

6. The optical absorbance meter according to claim 1, wherein the first optical aperture and/or the second optical aperture is constituted as a part of the main body of the optical absorbance meter and is adapted to fix the first and second closing member to the main body.

7. The optical absorbance meter according to claim 1, wherein at least one of the first optical aperture and the second optical aperture includes at least one of a light-interrupting and a light absorbing material which is formed on the first and second closing member by vapor-depositing, printing or coating by a masking technique.

8. The optical absorbance meter according to claim 1, wherein the introducing path for introducing liquid is provided with a diffusion path for mixing the introduced liquid.

9. The optical absorbance meter according to claim 1, wherein the first and second closing member comprise a convex lens.

10. The optical absorbance meter according to claim 1, wherein the first and second closing member comprise a flat light-transmission plate.

11. An optical absorbance meter including a constant cross-section flow passage for liquid to be tested, each end of which is closed with a respective first and second closing member, an introducing path for introducing liquid to the flow passage and a discharging path for discharging the liquid from the flow passage, wherein light from a light source is incident from one side near the first closing member and emits from the other side near the second closing member, the optical absorbance meter comprising:

a first optical aperture disposed in front of the first closing member at an incident side;

a second optical aperture disposed in rear of the second closing member at an emission side; and wherein an aperture diameter of the first optical aperture in a direction perpendicular to an axial line of the flow passage is smaller than a smallest diameter of the flow passage in the direction perpendicular to the axial line of the flow passage, and wherein an aperture diameter of the second optical aperture in the direction perpendicular to the axial line of the flow passage is larger than that of the first optical aperture.

12. The optical absorbance meter according to claim 11, which further comprises a light emission means composed of a sole light source at a light incident side, a light separating means for forming the spectrum of light emitted from the light emission means or a filtering means for permitting only a limited wavelength to pass, and a light receiving means for receiving light emitted from the flow passage to a light emission side.

13. The optical absorbance meter according to claim 11, which further comprises a light emission means composed of a sole light source at a light incident side, a light separating means for forming the spectrum of light emitted to a light emission side via the flow passage or a filtering means for permitting only a limited wavelength to pass, and a light receiving means for receiving the emitted light.

14. The optical absorbance meter according to claim 12, wherein the light receiving means is disposed so as to be inclined to the optical path of light emitted through the flow passage.

15. The optical absorbance meter according to claim 13, wherein the light receiving means is disposed so as to be inclined to the optical path of light emitted through the flow passage.

16. The optical absorbance meter according to claim 11, wherein the first optical aperture and/or the second optical aperture is constituted as a part of the main body of the optical absorbance meter and is adapted to fix the first and second closing member to the main body.

17. The optical absorbance meter according to claim 11, wherein at least one of the first optical aperture and the second optical aperture includes at least one of a light-interrupting and a light absorbing material which is formed on the first and second closing member by vapor-depositing, printing or coating by a masking technique.

18. The optical absorbance meter according to claim 11, wherein the introducing path for introducing liquid is provided with a diffusion path for mixing the introduced liquid.

19. The optical absorbance meter according to claim 11, wherein the first and second closing member comprise a convex lens.

20. The optical absorbance meter according to claim 11, wherein the first and second closing member comprise a flat light-transmission plate.

* * * * *